United States Patent
Mercati

(10) Patent No.: US 7,410,660 B2
(45) Date of Patent: Aug. 12, 2008

(54) PHARMACEUTICAL, NUTRACEUTICAL, DIETETIC AND NUTRITIONAL COMPOSITIONS BASED ON VEGETABLE FIBRES

(75) Inventor: Valentino Mercati, Sansepolcro (IT)

(73) Assignee: Aboca S.p.A. Societa' Agricola, Sansepolcro (AR) (IT)

( * ) Notice: Subject to any disclaimer, the term of this patent is extended or adjusted under 35 U.S.C. 154(b) by 0 days.

(21) Appl. No.: 11/324,287

(22) Filed: Jan. 4, 2006

(65) Prior Publication Data
US 2006/0147560 A1    Jul. 6, 2006

(30) Foreign Application Priority Data
Jan. 5, 2005  (IT)  .................... MI2005A0010

(51) Int. Cl.
*A61K 36/33*  (2006.01)
*A61K 36/05*  (2006.01)
*A61K 36/00*  (2006.01)

(52) U.S. Cl. .................... 424/767; 424/768; 424/725

(58) Field of Classification Search ........................ None
See application file for complete search history.

(56) References Cited

U.S. PATENT DOCUMENTS 5,498,436 A * 3/1996 Modliszewski et al. ..... 426/573
6,228,213 B1 * 5/2001 Hanna et al. .................. 162/18
2003/0138548 A1 * 7/2003 Bierer et al. ................ 426/630
2004/0126444 A1 * 7/2004 D'Huart et al. ............. 424/767
2004/0265398 A1 * 12/2004 Fleischner .................. 424/725

OTHER PUBLICATIONS

1998. Kossori et al. Composition of Pulp, skin, and seeds of prockly pears fruit. Plant Foods for Human Nutrition. 52: 263-270.*

* cited by examiner

*Primary Examiner*—Christopher R. Tate
*Assistant Examiner*—Melenie McCormick
(74) *Attorney, Agent, or Firm*—Young & Thompson

(57) ABSTRACT

Pharmaceutical, nutraceutical, dietetic and nutritional compositions containing:
a) glucomannan,
b) *Opuntia ficus indica*,
c) microcrystalline cellulose
present a high gastrointestinal swelling index, which induces an immediate feeling of fullness, release of cholecystokinins and slowing of gastric voiding that prolongs the feeling of fullness. Associating the complex of three vegetable fibers with a mixture of freeze-dried mucilages increases its gastrointestinal swelling properties.

13 Claims, No Drawings

PHARMACEUTICAL, NUTRACEUTICAL, DIETETIC AND NUTRITIONAL COMPOSITIONS BASED ON VEGETABLE FIBRES

FIELD OF INVENTION

This invention relates to pharmaceutical, nutraceutical, dietetic and nutritional compositions containing:
a) glucomannan,
b) *Opuntia ficus indica,*
c) microcrystalline cellulose.

These compositions present a high swelling index at gastrointestinal level which produces an immediate feeling of fullness, release of cholecystokinins, and slowing of gastric emptying which prolongs the feeling of fullness. Associating the complex of three vegetable fibres with a mixture of freeze-dried mucilages increases its swelling properties in the gastrointestinal area.

PRIOR ART

Dietary Fibres

Dietary fibres are defined as "substances of vegetable origin which are not hydrolysable by the enzymes secreted by the human digestive apparatus, are only partly hydrolysable by the intestinal bacterial flora, and are classified under the following categories: cellulose, modified cellulose, hemicellulose, pectins, vegetable gums, mucilages and lignin". In view of their "indigestibility", due to the inability of the enzymes of the human digestive apparatus to break down the polysaccharide chains of which they are made into simpler components (monosaccharides) that can be assimilated by the body, fibres possess virtually no nutritional or energy value, but during their transit through the digestive tract perform a series of functional and metabolic actions that are essential to the normal intestinal function and very useful for the health of the whole body in general.

Consequently, dietary fibre has become well known as an essential component of the diet, and numerous epidemiological studies demonstrate that populations whose diet is rich in vegetable fibres are less subject to constipation, many other common disorders of the digestive apparatus (colitis, flatulence, diverticulitis, etc.) and metabolic disorders (obesity, dyslipidaemia and diabetes) than populations whose diet is characterised by a low dietary fibre content. Frequent consumption of dietary fibre, combined with a diet rich in vegetables, cereals and fruit, has also been associated with a reduction in the risk of tumours of the digestive apparatus, especially colorectal cancer.

Dietary fibre consists of a highly complex set of vegetable compounds constituted by long polysaccharide chains polymerised through $\alpha$ and $\beta$ glycoside bonds, which differ according to the type of glycoside bond that joins them, the length of the chain, the type of recurrent saccharide unit and the degree of branching.

The various components of dietary fibre can be classified according to their behaviour in water as:
  soluble fibres: mainly polysaccharides characterised by high solubility and a more or less marked ability to form viscous, gel-like solutions.
  insoluble fibres: which do not greatly modify their structure on contact with water, although they can retain much of it by increasing their mass; they mainly act as swelling agents, giving rise to what is commonly known as the "ballast effect".

When placed in water or aqueous solutions, soluble fibres tend to establish "points of contact" between the various segments of the polysaccharide chains, forming three-dimensional organised structures like a sort of "natural gel", which are highly viscous and absorbent, and retain much of the surrounding liquid phase and any solutes dissolved in it. The efficacy of soluble fibres in weight control is based on their ability, when hydrated, to form a thick, voluminous natural gel that binds to and retains a proportion of the food eaten (especially sugars and fats), which is then eliminated with the faeces (together with the fibres) at the end of digestion, without contributing in any way to the calorie content of the meal.

This ability to reduce food absorption takes place through two different, complementary mechanisms: the first is determined by the "mechanical" action of the gel (which traps liquids and dissolved nutrients in its lattice by adsorption), while the second is due to the ability of fibres to increase the viscosity of the digestive contents and consequently slow the rate of absorption of nutrients by the intestinal villi, hindering the diffusion processes and reducing the absorption of nutrients. As another consequence of fibre intake is reduced transit time through the intestine of digested material (which "glides" much faster thanks to the natural gel formed by the fibres), the absorption time is also reduced.

In addition to reducing food absorption, fibres cause a prolonged feeling of fullness due not only to the increased volume caused by swelling of the fibres in the gastrointestinal tract, but above all to the viscosity-controlling effect on the intestinal contents, which slows the glucose assimilation process, with the result that the postprandial glucose peak appears and disappears much more slowly.

For all the reasons described above, dietary fibres are widely used as adjuvants in low-calorie diets and as fibre supplements. Products based on dietary fibre currently on the market include CM3, a medical device based on highly crosslinked cellulose; Normaline Herbs, based on glucomannan and cellulose; Forlip, based on *opuntia*, chitosan and cellulose; and Dicoplus 100, based on glucomannan. A product called SyndRx, containing glucomannan and *opuntia* and indicated for blood glucose control, is also marketed in the USA.

Chemico-Physical Properties of Fibres

The physiological properties of a polysaccharide are partly predictable on the basis of chemico-physical properties such as fermentation, water retention ability, viscosity, and binding to bile acids.

WBC (water binding capacity). This is the quantity of water that the system does not release when subjected to physical stress such as centrifugation. It is a parameter influenced by the pH, ionic strength and microstructure of the gel.

WHC (water holding capacity). Defined as the quantity of water that the system traps in the lattice when it is not subjected to physical stress, and directly correlated with the moisture present in the system.

Ability to absorb and adsorb organic material: the ability of some soluble fibres to trap in their matrix gel-like organic molecules such as bile acids, sterols, toxic compounds and other waste materials removed from the human body.

Ion-exchange capacity: fibre acts as a weak ion-exchange resin due to the large number of free carboxyl groups present in saccharide residues, and the uronic acid content of the polysaccharide.

Gel formation: soluble fibres placed in water give a viscous gel-like structure, characterised by a three-dimensional solid macromolecular lattice able to retain the liquid phase.

Solubility and viscosity: The majority of polysaccharides exist in solution as disorderly coils or "tangles" which, after reaching the critical concentration, are dispersed in liquid and interact with the adjacent molecules, creating substantial flow resistance. The viscosity is associated with prolonged gastric voiding and increased transit through the small intestine. The slower gastric voiding is plausibly due to various factors, such as the increased volume of high-viscosity polysaccharides in the gastric environment, which causes distension of the stomach walls. This distension generates an increased release of cholecystokinins (CCK), which in turn slows gastric voiding. Moreover, the increased release of CCK may be related to reduced absorption and digestion of fats when high-viscosity polysaccharides are ingested.

WHC and WBC refer to the ability of a fibre to swell when placed in an aqueous medium and to retain water in its matrix under static or dynamic conditions. High-viscosity polysaccharides usually have high WHC/WBC values; in the small intestine they increase the total volume of the intestinal contents, especially the volume of the aqueous phase, thus diluting the concentration of the nutrients absorbed from the aqueous phase, and slowing the absorption rate. The expansion of the aqueous phase in the small intestine can also help to slow the rate of absorption of lipids, which are not soluble in the aqueous phase but form micelles that allow their transport through this phase to the cell surface.

A high WHC/WBC value allows penetration of water-soluble or hydrophilic substances into the fibre matrix, reduces its diffusion at the cell surface, and thus helps to reduce the availability of nutrients for absorption. In the large intestine, this phenomenon allows micro-organisms to penetrate into the fibre matrix and thus provide more access to digestion of the polysaccharides by micro-organisms (prebiotic effect).

Although WHC can represent a more real value than the quantity of water trapped in the system, there are physical limitations on the determination of said value. In fact, the sample must attain conditions of balance, which must be defined and standardised for each single raw material, and differ on variation of the dimensional distribution for the same raw material. For these reasons, WBC is used as fibre-characterising parameter. WBC is time-independent because the conditions of balance are achieved when the system is above the saturation limit, by inserting excess solvent in the system. A variety of factors affect the WBC of a fibre: interactions with the solute, the capillary suction forces and the forces of surface interaction.

Different methods for calculating WBC exist: the Baumann apparatus, absorption isotherms, and the centrifugation method. Each of them operates through its own water uptake mechanism. The Baumann determination is based on the uptake of water through the action of forces of capillarity in conjunction with the swelling of the fibres. Water absorption isotherms are based on steam uptake. The determination by centrifugation reflects the combined effect of a first absorption of water by the fibre, which allows swelling, and subsequently the application of a centrifugal force to the fibre-water system. The centrifugation method can be considered the best choice for calculating the WBC of the raw materials included in a system with high water activity (Aw>0.98) as in the case of the dispersion created in the gastric environment after the disintegration of the tablets. In fact the raw materials considered are "saturated" with water, and the centrifugation test can be likened to an accelerated way of achieving that state of "saturation".

DESCRIPTION OF THE INVENTION

It has now been found pharmaceutical, nutraceutical, dietetic and nutritional compositions containing:

a) glucomannan, b) *Opuntia ficus indica,* c) microcrystalline cellulose present a high gastrointestinal swelling index, which induces an immediate feeling of fullness, release of cholecystokinins and slowing of gastric voiding that prolongs the feeling of fullness.

It has been found that the addition of a mixture of freeze-dried mucilages to the compositions according to the invention increases its gastrointestinal swelling properties.

*Opuntia* (*Opuntia ficus indica*) or Nopal is a cactus originating from the tropical zones of America. Its active constituents are contained in the cladodes, and are constituted by mucilaginous substances, fibres, proteins and mineral salts. In traditional Mexican medicine, preparations based on *opuntia* leaves are used to treat diabetes. In recent years, numerous studies have demonstrated hypoglycaemic activity, a beneficial action on other metabolic disorders such as obesity and hyperlipidaemia, a satiating effect, and anti-inflammatory, digestive and painkilling properties. The active ingredient is constituted by the flesh of the dehydrated cladodes, picked from plants at least 4 years old; after elimination of the spines, the cladodes are cut into thin slices, dried until completely dry, and finally minced to the required micronisation. The dried product presents as a fine, pale green powder. It is a wholly natural raw material which, due to its high dietary fibre content, can make a valuable contribution to the overall balance of the diet.

Glucomannan is a soluble dietary fibre consisting of a hydrocolloidal polysaccharide based on D-glucose and D-mannose residues bound to one another by beta 1-4 bonds. Glucomannan is obtained by grinding the tuber of *Amorphophallus konjac*, a species which only grows in certain areas such as China and Japan, where it is traditionally used as a foodstuff.

Cellulose is a source of insoluble fibre, deriving from hydrolysis of cellulose pulp in an acid environment. It consists of a linear polymer of glucose molecules bound by beta 1-4 bonds which cannot be attacked by intestinal amidolytic enzymes. It is highly insoluble, and represents the main constituent of cereal bran.

Mucilages belong to the group of soluble fibres, in this case originating from edible seeds of species of the Linaceae family (*Linum usitatissimum*) and the roots, leaves and flowers of Malvaceae (marsh mallow) and Tiliaceae (lime). The freeze-dried extracts, produced by aqueous extraction of the active ingredient and subsequent freeze-drying, are particularly rich in soluble fibre, especially mucilages.

More particularly, the pharmaceutical, nutraceutical, dietetic and nutritional compositions to which this invention relates contain the various constituents in the following concentration ranges:

a) Glucomannan from *Amorphophallus konjac* between 30 and 70%;
b) *Opuntia ficus indica* between 10 and 50%;
c) Microcrystalline cellulose between 20 and 50%.

According to a preferred aspect, *Opuntia ficus indica* is present in the form of dehydrated stalk pulp.

According to a preferred aspect, the compositions according to the invention will also contain a mixture of mucilages in a concentration range of between 1 and 10%.

According to a preferred aspect, the mixture of mucilages is constituted by freeze-dried mucilages originating from flax seeds (*Linum usitatissimum*), marsh mallow root (*Althea officinalis*) and lime flowers (*Tilia platyphyllos*).

The various components of the compositions according to the invention present the following characteristics:

Glucomannan is able to hydrate and swell, forming highly viscous gel-like aqueous solutions which are stable in an acid environment. The increased viscosity influences the gastric voiding time, leading to a prolonged feeling of fullness.

Cellulose produces the "ballast effect", with increased weight of the faeces, increased intestinal transit rate, increased intraluminal colon pressure and reduced absorption of fat globules and bile salts, which remain trapped in the fibrous lattice.

*Opuntia ficus indica* contains soluble fibres (especially pectins) able to increase their viscosity in an acid environment, and insoluble fibres (especially cellulose and hemicellulose).

Flax, lime and marsh mallow mucilages are also able to hydrate and form similar gel systems.

In an acid environment, *opuntia* forms a lattice of fibrous material much larger than that which it tends to form at a neutral pH. The expansion of this lattice also structurally involves the glucomannan, mucilage and cellulose fibres, so as to increase the surface and consequently the water binding sites of each constituent, resulting in a synergic effect in terms of WBC. An increase in the volume occupied and the water retained by the complex of fibres is obtained.

Consequently, the compositions according to the invention present, in terms of swelling index and WBC, an effect greater than the sum of the effects obtained after separate administration of the individual constituents of the association, due to a synergic effect between the constituents of the composition.

A particularly interesting synergic effect, with a swelling index of 150% and a WBC of 140% more than the sum of the contributions of the individual components, is obtained when the various constituents are present in the following proportions:

| | |
|---|---|
| a) Glucomannan from *Amorphophallus konjac* | 40 ± 5% |
| b) *Opuntia ficus indica* dehydrated stalk pulp | 27 ± 5% |
| c) Microcrystalline cellulose | 30 ± 5% |
| d) Mixture of mucilages | 3 ± 2% |

Thus, according to a particularly preferred aspect, the compositions according to the invention will contain the various constituents in the proportions indicated above.

The compositions according to the invention, which supply WBC and swelling index values exceeding those obtainable from the mere sum of the individual ingredients, give rise to a viscous gelified system of larger size, which is responsible for the beneficial action of the fibres on the gastrointestinal system. Due to the distension of the stomach, the swelling effect generates an immediate increase in the feeling of fullness (due to direct stimulation of the vagus nerve) and the release of cholecystokinins (local hormones secreted by the stomach and the upper part of the small intestine), which slows gastric voiding and prolongs the feeling of fullness. The water-binding capacity (WBC) of the fibres also increases the volume of the intestinal contents, which slows the rate of absorption of the nutrients. Consequently, intake of the compositions according to the invention a few minutes before the main meals helps to reduce/attenuate the feeling of hunger in the stomach and leads to lower absorption of food in the intestine.

The compositions according to the invention could be formulated suitably for oral administration, and will be prepared according to conventional methods well known in pharmaceutical technology, such as those described in Remington's Pharmaceutical Handbook, Mack Publishing Co., N.Y., USA, using excipients, diluents, fillers and anti-caking agents acceptable for their final use. Examples of these formulations include tablets, chewable tablets, diet bars, suspensions and the like.

The compositions according to the invention could also contain additional constituents with complementary or otherwise useful activity. Examples of such constituents are powders and/or extracts originating from plants such as chicory, and essential oils such as star aniseed and fennel.

Some examples of compositions according to the invention are set out below.

EXAMPLE 1

Composition A

| Ingredients | % |
|---|---|
| Glucomannan | 41.7 |
| Microcrystalline cellulose | 30.8 |
| *Opuntia ficus indica* | 27.5 |

EXAMPLE 2

Composition B

| Ingredients | % |
|---|---|
| Glucomannan | 40.8 |
| Microcrystalline cellulose | 30.2 |
| *Opuntia ficus indica* | 26.8 |
| Mixture of freeze-dried mucilages | 2.2 |

EXAMPLE 3

Composition in 680 mg Tablets

| Ingredients | |
|---|---|
| Glucomannan from *Amorphophallus konjac* tuber | 258.4 mg |
| Microcrystalline cellulose | 191 mg |

-continued

| Ingredients | |
|---|---|
| *Opuntia* powdered stalk pulp | 170 mg |
| Flax seeds, freeze-dried mucilages | 4.8 mg |
| Lime flowers, freeze-dried mucilages | 4.8 mg |
| Marsh mallow flowers, freeze-dried mucilages | 4.8 mg |
| Chicory root inulin | 27.2 mg |
| Flavouring | 17 mg |
| Fennel essential oil | 1 mg |
| Star aniseed essential oil | 1 mg |

EXAMPLE 4

Composition in 4 g Sachets

| Ingredients | |
|---|---|
| Glucomannan from *Amorphophallus konjac* tuber | 1.02 g |
| Microcrystalline cellulose | 755 mg |
| *Opuntia* powdered stalk pulp | 670 mg |
| Flax seeds, freeze-dried mucilages | 18.3 mg |
| Lime flowers, freeze-dried mucilages | 18.3 mg |
| Marsh mallow flowers, freeze-dried mucilages | 18.3 mg |
| Maltodextrins | 1 g |
| Flavourings | 0.5 g |

The compositions according to the invention were subjected to water-binding capacity (WBC) and swelling index tests.

1. Water-Binding Capacity Test

Measurement of WBC allows evaluation of the quantity of water which can be bound by a single raw material or a mixture of raw materials, in an acid environment (similar to the gastric environment).

Method: 20 g of a solution at pH=2 (acidified with HCl) is added to 0.5 g of the dry substance. Agitate until a homogenous suspension is obtained, then leave to stand for 30 mins, to allow absorption of the water by the body and the corresponding swelling. The suspension is centrifuged for 30 minutes at 4000 RPM and the pellet is separated from the supernatant. The ability to bind water will be equal to the weight of the pellet minus the water retained by the blank. The value obtained is divided by the total weight of the anhydrous sample. The results are set out in Table 1.

TABLE 1

| Sample | Legend code | WBC (g/g) Experimental | WBC (g/g) Theoretical | Synergy |
|---|---|---|---|---|
| Glucomannan | A | 18.85 | | |
| Microcrystalline cellulose | B | 2.3 | | |
| *Opuntia ficus indica* | C | 3.2 | | |
| Flax seeds, freeze-dried mucilages | D | 6.5 | | |
| Marsh mallow root, freeze-dried mucilages | E | 1 | | |
| Lime flowers, freeze-dried mucilages | F | 2.7 | | |
| Composition A | G | 21 | 9.5 | +121% |
| Composition B | H | 23 | 9.4 | +144% |

2. Swelling Index

The measurement is performed with deionised water at a neutral pH, according to the method laid down in the Official Pharmacopoeia 11th Ed. The degree of subdivision of the raw material is that which will be present in the product at a later stage. The swelling index is the volume in millilitres occupied by 1 g of active ingredient, with the mucilage sticking to it, after leaving it to swell in aqueous liquid for 4 h. The results are set out in Table 2.

TABLE 2

| Sample | Code | Quantity of active ingredient | Quantity of solvent | Experimental swelling index | Theoretical swelling index | Synergy |
|---|---|---|---|---|---|---|
| Glucomannan | A | 1 g | 100 ml | 75 | | |
| Opuntia | B | 1 g | 100 ml | 20 | | |
| Cellulose | C | 1 g | 100 ml | 0 | | |
| Mixture of freeze-dried mucilages | D | 1 g | 100 ml | 0 | | |
| COMPOSITION A | E | 1 g | 100 ml | 89 | 37 | +140% |
| COMPOSITION B | F | 1 g | 100 ml | 96 | 37 | +160% |

The invention claimed is:

1. A pharmaceutical, nutraceutical, dietetic or nutritional composition for decreasing body weight comprising;
   a) 40±5% by weight of glucomannan from *Amorphophallus konjac;*
   b) 27±5% by weight of *Opuntia ficus indica* cladodes; and
   c) 30±5% by weight of microcrystalline cellulose.

2. The composition as claimed in claim 1, wherein the *Opuntia ficus indica* cladodes are present in the form of dehydrated stalk pulp.

3. The composition as claimed in claim 1, further comprising
   d) a mixture of freeze-dried mucilages.

4. The composition as claimed in claim 3, wherein the mixture of freeze-dried mucilages is present in a concentration range of between 1 and 10% by weight of the composition.

5. The composition as claimed in claim 4, wherein the mix of freeze-dried mucilages is present in a concentration range of 3±2% by weight of the composition.

6. The composition as claimed in claim 3, wherein the mixture of freeze-dried mucilages originates from flax seeds (*Linum usitatissimum*), marsh mallow root (*Althea officinalis*), and lime flowers (*Tilia platyphyllos*).

7. The composition as claimed in claim 1, wherein the *Opuntia ficus indica* cladodes are in powdered form.

8. The composition as claimed in claim 1, wherein only the glucomannan, the *Opuntia ficus indica* cladodes, the microcrystalline cellulose, and, optionally, a mixture of freeze-dried mucilages are active ingredients of the composition.

9. The composition as claimed in claim 1, wherein said composition is for human consumption.

10. A method for the preparation of a pharmaceutical, nutraceutical, dietetic or nutritional composition, comprising: adding
   a) 40±5% by weight of glucomannan from *Amorphophallus konjac*,
   b) 27±5% by weight of *Opuntia ficus indica* cladodes, and
   c) 30±5% by weight of microcrystalline cellulose, and optionally
   d) a mixture of freeze-dried mucilages
   to a pharmaceutical, nutraceutical, dietetic, or nutritionally acceptable vechicle.

11. The method as claimed in claim 10, wherein the *Opuntia ficus indica* cladodes are in powdered form.

12. The method as claimed in claim 10, further comprising:
   cutting the *Opuntia ficus indica* cladodes into thin slices;
   drying the slices; and
   mincing the slices to form an *Opuntia ficus indica* cladodes powder before adding the *Opuntia ficus indica* cladodes to the acceptable carrier.

13. A method for decreasing body weight, comprising:
   administering an effective amount of a pharmaceutical, nutraceutical, dietetic or nutritional composition according to claim 1, to a subject in need thereof, wherein,
   the effective amount increases a feeling of fullness in the subject and decreases absorption of nutrients by the subject so that body weight is decreased.

* * * * *